United States Patent [19]

Battifora

[11] Patent Number: 4,820,504

[45] Date of Patent: Apr. 11, 1989

[54] MULTI-SPECIMEN TISSUE BLOCKS AND SLIDES

[75] Inventor: Hector A. Battifora, Arcadia, Calif.

[73] Assignee: City of Hope, Duarte, Calif.

[21] Appl. No.: 11,689

[22] Filed: Feb. 6, 1987

Related U.S. Application Data

[63] Continuation-in-part of Ser. No. 828,775, Feb. 12, 1986, abandoned.

[51] Int. Cl.$^4$ ............... G01N 1/28; G01N 33/531; G01N 33/577
[52] U.S. Cl. .................................. 424/3; 436/527; 436/543; 436/548
[58] Field of Search ................. 424/3; 436/174, 176, 436/178, 503, 527, 548, 813, 543

[56] References Cited

U.S. PATENT DOCUMENTS 4,647,543  3/1987  Stöcker .................................. 424/3

OTHER PUBLICATIONS

Lillie, *Histopathologic Technic and Practical Histo Chemistry*, 3rd ed., McGraw-Hill Book Company, New York, 1965, pp. 74-77.
Mason et al., in Bullock et al., (EDS.) *Techniques in Immunocytochemistry*, vol. 2, Academic Press, New York, 1983, pp. 175-216.
Nairn, *Fluorescent Protein Tracing*, 4th Ed. Churchill Livingstone, Edinburgh, 1976, pp. 131-147 and 375-377.
Stein et al., *Lab Invest.*, 52, 676-683, 1985.
G. D. Johnson et al., in D. M. Weir (ED.), *Handbook of Experimental Immunology*—3rd ed., Blackwell Scientific Pub, Oxford, 1978, pp. 15.3 and 15.4.

*Primary Examiner*—Robert J. Warden
*Assistant Examiner*—David A. Saunders
*Attorney, Agent, or Firm*—Edward S. Irons

[57] ABSTRACT

A method of preparing a multi-specimen tissue block, and sections thereof, comprising forming a plurality of different antigenically reactive tissue specimens into rods having a relatively small cross-sectional area and a relatively great length, disposing the rods in a substantially parallel relationship on a casing, wrapping the rods in the casing, embedding the wrapped rods in an embedding medium to form a tissue block in which the rods are perpendicular to the face of the block, and dividing the block into sections which each contain a cross-section of each of the rods.

37 Claims, 5 Drawing Sheets

MULTI-SPECIMEN TISSUE BLOCKS AND SLIDES

This application is a continuation-in-part of application Ser. No. 828,775 filed Feb. 12, 1986 now abandoned.

BACKGROUND OF THE INVENTION

This invention relates to tissue blocks having a plurality of different antigenically reactive tissues embedded therein, sections of such blocks, slides prepared from such sections, and the use of such slides in immunohistologic procedures.

In recent years, rapid progress in the application of immunohistochemical methods to histopathologic diagnosis has been stimulated by the advent of monoclonal antibodies. Present monoclonal antibody technology is inefficient, however, because it often yields many more useless monoclonal antibodies than useful ones. The screening of such antibodies to identify the clinically useful ones therein is laborious, time consuming and expensive.

Immunohistologic screening is practical only if a large number of tissues can be grouped within a small surface area, because only a limited amount of hybridoma supernatant is available in the early phase of monoclonal antibody generation when rapid colony selection decisions must be made. Recognized screening techniques usually employ slides, each containing only a single specimen. A single slide made according to the present invention may provide one hundred or more different tissue specimens and/or neoplasms, all of which can be simultaneously screened by application of a single drop of reagent such as a hybridoma supernatant. Because all of the tissue specimens are treated equally during immunostaining, most sources of variation are removed and comparative studies are facilitated. See, Battifora, H., "The Multitumor (Sausage) Tissue Block: Novel Method for Immunohistochemical Antibody Testing", *Laboratory Investigation*, 55:244 (1986).

SUMMARY OF THE INVENTION

In general, the invention features a method of preparing multi-specimen tissue blocks comprising disposing a plurality of different antigenically reactive tissue specimens in the shape of rods having greater length than width in substantially parallel relationship on a casing; wrapping the specimen rods in the casing to form a specimen rod bundle; embedding the specimen rod bundle in embedding medium to provide a multi-sample tissue block; and slicing the block to provide a plurality of sections each comprising a transverse cross-section of each of the tissue specimen rods of the specimen rod bundle.

Sections of such tissue blocks can be used to prepare slides useful in various immunohistochemical methods. One of the advantages of the invention is that clinically useful monoclonal antibodies can be easily identified without great expense during early phases of monoclonal antibody production. Because the tissue blocks can be prepared to include tissue specimens with a broad spectrum of antigen densities, the tissue blocks of this invention are advantageous for the routine monitoring of sensitivity in immunohistochemistry.

Other features and advantages of the invention will be apparent from the following description of the preferred embodiments, and from the claims.

DESCRIPTION OF THE DRAWINGS

FIG. 10(*a*) shows an actual stained tissue block section having a different form of compartment formed by segmenting the specimen rod bundle as it is wrapped in its casing to create several partitioned groups of specimen rods;

FIG. 10(*b*) shows a map of the tissue block section of FIG. 10(*a*) with printed identification labels placed on the appropriate groupings of specimen rods;

As appears from inspection, at least 50 tissue specimens can be counted in FIG. 10(*a*) and at least 89 specimens in FIG 11; whereas, FIGS. 13 to 16 show 71, 49, 41 and 88 tissue specimens, respectively.

DESCRIPTION OF THE PREFERRED EMBODIMENTS

Figure 1:
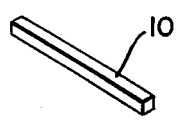
FIG. 1 is a schematic perspective view of a specimen rod of this invention.

A plurality of different antigenically reactive tissue specimens are cut into slender rod-like pieces (rods) of relatively greater length than width and which have a thickness of approximately one millimeter. Typical specimen rods may range from approximately 8 to 12 millimeters in length, and preferably are about 10 millimeters in length, from about 0.5 to about 1.5 millimeters in width, and approximately one millimeter in thickness to provide a transverse cross-section of approximately 0.75 to about 1.5 millimeters, and are preferably about one square millimeter.

The specimen rods may be prepared either from conventionally fixed tissue specimens, tissue specimens fixed in special fixatives, or from unfixed, preferably freeze-dried tissue specimens. If tissue specimens are to be eventually freeze-dried, they should be snap-frozen.

The fixation of tissue specimens is accomplished by cutting the tissue specimens in thicknesses that are easily penetrated by fixing fluid in a relatively short amount of time.

Examples of fixing fluids are aldehyde fixatives such as formaldehyde, formalin or formol, glyoxal, glutaraldehyde, hydroxyadipaldehyde, crotonaldehyde, methacrolein, acetaldehyde, pyruic aldehyde, malonaldehyde, malialdehyde, and succinaldehyde; chloral hydrate; diethylpyrocarbonate; alcohols such as methanol and ethanol; acetone; lead fixatives such as basic lead acetates and lead citrate; mercuric salts such as mercuric chloride; formaldehyde sublimates; sublimate dichromate fluids; chromates and chromic acid; and picric acid. Heat may also be used to fix tissue specimens by boiling the specimens in physiologic sodium chloride solution or distilled water for two to three minutes. Whichever fixation method is ultimately employed, the cellular structures of the tissue specimens must be sufficiently hardened before they are embedded in a medium such as paraffin.

The individual tissue specimens used to prepare the specimen rods are embedded in embedding media such as paraffin or other waxes, gelatin, agar, polyethylene glycols, polyvinyl alcohol, celloidin, nitrocelluloses, methyl and butyl methacrylate resins or epoxy resins which are polymerized after they infiltrate the specimen. Water soluble embedding media such as polyvinyl alcohol, carbowax (polyethylene glycols), gelatin, and agar, may be used directly on specimens. Water-insoluble embedding media such as paraffin and nitrocellulose require that specimens be dehydrated in several changes of solvent such as ethyl alcohol, acetone, or isopropyl alcohol and then be immersed in a solvent in which the embedding medium is soluble. In the case where the embedding medium is paraffin, suitable solvents for the paraffin are xylene, toluene, benzene, petroleum, ether, chloroform, carbon tetrachloride, carbon bisulfide, and cedar oil. Preferably a tissue specimen is immersed in two or three baths of the paraffin solvent after the tissue is dehydrated and before the tissue specimen is embedded in paraffin.

In one embodiment of the present invention the specimen rods are prepared from selected antigenically reactive tissue specimens which have been fixed and pre-embedded in blocks of an embedding medium such as paraffin. See generally, Lillie, R. D., et al., "Histopathologic Technic and Practical Histochemistry" (4th Ed.) 1976, McGraw-Hill for details of fixing, slicing, embedding, and staining specimens. In general, the specimens are removed from their paraffin blocks, deparaffinized in a solvent such as xylene, rehydrated in a solvent such as ethanol to a final concentration of 50%, and then cut into rods.

In one of the other embodiments of the present invention, tissue specimens which are to be eventually cut into specimen rods may be freeze-dried without being fixed. The use of freeze-dried specimens in accordance with this invention is preferable to using conventionally fixed specimens.

The reason why freeze-dried tissue specimens are usually preferred is that while sections of the tissue blocks that contain conventionally fixed antigenic specimens optimize the search for monoclonal antibodies which perform well in immunohistochemistry, an attendant disadvantage is that monoclonal antibodies recognize a single epitope and hence are particularly sensitive to adverse effects of fixation. If a particular epitope is damaged or masked by the fixative, the monoclonal antibody will not recognize the antigen. Another problem associated with screening monoclonal antibodies with fixed tissues by immunohistochemistry is that such antibodies may still fail to recognize the native antigen in vivo. Thus, such antibodies may be of little value for clinical applications which require parenteral administration of the monoclonal antibody such as, for example, imaging and immunotherapy of neoplasms.

However, monoclonal antibodies which fail to identify antigens in fixed tissues which have altered antigenic reactivity perform well with unfixed freeze-dried tissues because many of the diagnostically relevant marker substances or antigens are conserved in a manner that permits their identification by immunohistochemical methods. See, e.g., Stein, H., et al., "Use of Freeze-Dried Paraffin-Embedded Sections for Immunohistologic Staining with Monoclonal Antibodies", *Laboratory Investigation,* 52:676 (1985).

Tissue specimens are freeze-dried by deep freezing in plastic tissue cassettes and storing them at $-70°$ C. The cassettes are freeze-dried in a modified freeze-drying machine, as described below, at temperatures below 30° C. for a period of between about 48 hours and about 120 hours. While in the vacuum created by the freeze-dryer, the tissues are exposed to an organic solvent such as xylene, chloroform, or toluene, for the purpose of removing the lipids in order to render the tissues permeable for the embedding medium. The freeze-dried defatted tissues are embedded in paraffin by conventional means as described herein. These freeze-dried, paraffin-embedded, tissues can now be used as sources of tissue samples for the preparation of multi-specimen tissue blocks.

Preferably, a modified conventional freeze-drying machine is used to practice this invention. The main tube connecting the refrigerated vacuum portion of a conventional machine to a receptacle containing the tissue specimens is fitted with a valve that functions to open and close the connection. A conduit connected to a solvent container is fitted to the main tube between the valve and the specimen receptacle. Flow of solvent through the conduit is controlled by an appropriate valve.

The specimen receptacle was kept in ice during the freeze-drying procedure. The specimens were put under vacuum pressure by opening only the valve in the main tube while maintaining the valve in the solvent conduit closed. After the tissue specimens were under vacuum, the valve in the main tube was closed, thereby maintaining the vacuum in the specimen receptacle. The valve in the solvent conduit was then opened, and the pressure differential between the main receptacle and the solvent receptacle caused the solvent to flow from the solvent receptacle through the solvent conduit and the main tube into the specimen receptacle.

The appropriately treated fixed or freeze-dried, unfixed tissue samples are then embedded in embedding media by filling a receptacle containing the tissue specimen with embedding media and then cooling or polymerizing the mass. If a sausage containing a plurality of specimen rods is to be embedded, the sausage must be oriented such that the specimen rods are perpendicular to the face of the block.

Paraffin embedded tissue specimens which are to be cut into specimen rods, are dewaxed by immersion in a solvent such as xylene and then rehydrated in ethanol at a graded series of concentrations to a final concentration of 50%. Such hydrated tissue is then cut with a sharp knife or razor blade or an automatic tissue slicer into approximately 1 mm thick slices. These slices are then cut into rods 10 having a cross-sectional area, preferably of about 1 mm$^2$ and a length of about 10 mm, as shown in FIG. 1.

Figure 2:
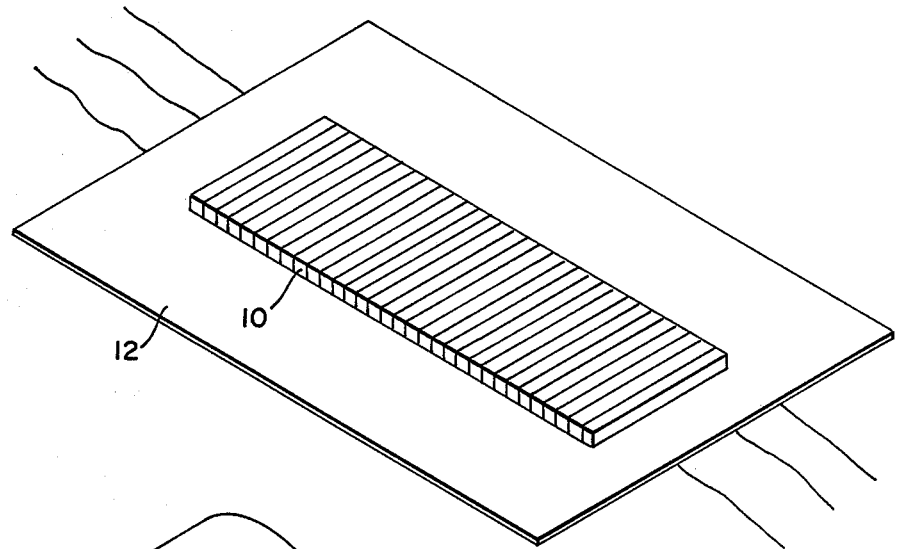
FIG. 2 is a schematic perspective view of a casing having a plurality of specimen rods disposed in parallel thereon.

A plurality of specimen rods 10, for example one hundred or more, are disposed in a substantially parallel, closely packed arrangement on a casing 12 shown in FIG. 2. The casing may consist of any suitable material and is preferably a portion of a small intestine of a small mammal such as a rabbit, which may be stretched, fixed in formalin, and stored in 50% ethanol in known manner. Alternatively, the casing may cellulosic synthetic resinous material such as polyethylene, polypropylene, polyethylene terephthalate, or an equivalent organic sheet material.

Figure 3:
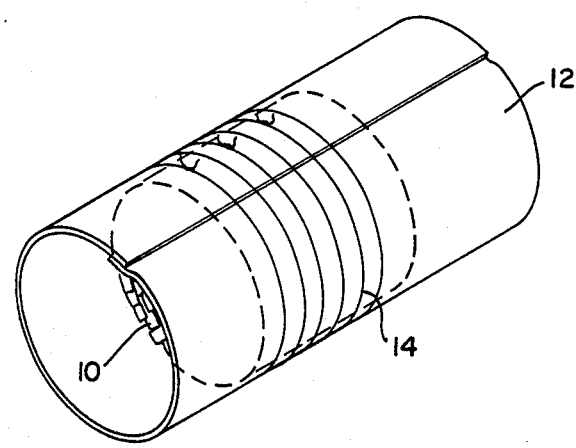
FIG. 3 is a schematic perspective view of the arrangement shown in FIG. 2 after the specimen rods have been tightly wrapped in the casing and the casing secured by binding it with a fine thread to provide a specimen rod bundle or "sausage".
Figure 4:
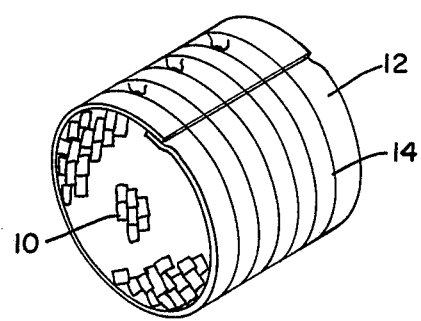
FIG. 4 is a perspective view of the "sausage" shown in FIG. 3 with the ends cut away to expose the specimen rods in transverse cross-section.

As shown in FIG. 3, after the specimen rods 10 have been disposed on casing 12, preferably in a closely stacked and substantially parallel relationship, the casing 12 is wrapped around the rods and a specimen rod bundle or "sausage" is produced which is secured with any appropriate means 14 such as a fine thread. It has been found that the best results are obtained when a greater pressure is applied to the stack of specimen rods as they are rolled in the casing to form a tightly wrapped rod bundle or sausage. At least one end of the sausage is then cut off to expose the ends of each of the rods 10 in transverse cross-section as shown in FIG. 4.

Figure 5:
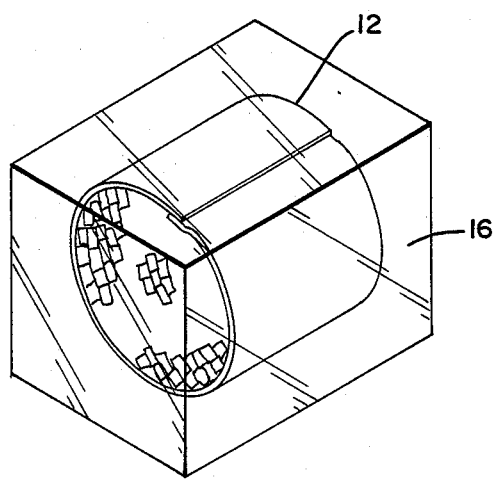
FIG. 5 is a perspective view of the trimmed "sausage" shown in FIG. 4 after the thread has been removed and the "sausage" has been embedded in an embedding medium such as paraffin.

As shown in FIG. 5, after thread 14 is removed, the rod bundle or sausage is embedded in paraffin or other suitable embedding media in conventional manner as discussed above, to produce a multi-sample tissue block 16 in which the specimen rods 10 are perpendicular to the face of block 16.

Figure 6:
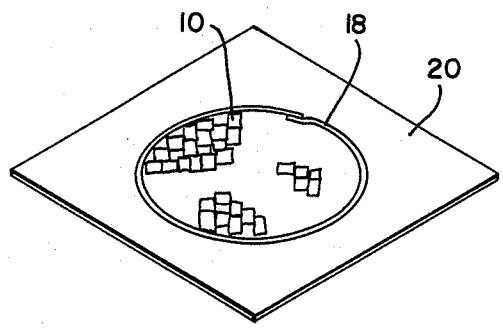
FIG. 6 is a perspective view of a section of the embedded sausage shown in FIG. 5.
Figure 7:
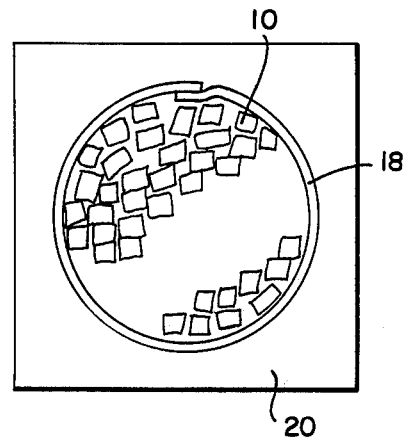
FIG. 7 is an elevational view of one of the sections shown in FIG. 6 and schematically illustrates the casing and the specimen rods within the casing.

Sections 18 of the tissue block 16 are produced by slicing the tissue block thinly into sections having a thickness of from about 2.5$\mu$ to about 10$\mu$ with a microtome or similar instrument. Between 750 and 1000 5 $\mu$thick sections can be prepared from an average size block. Slides 20 as shown in FIGS. 6 and 7 are prepared from the block sections 18 using conventional techniques. If care is taken to keep all of the rods in a substantially straight, parallel stack during preparation of the tissue blocks, sections of such tissue blocks and slides comprising such sections have a plurality of almost identically positioned tissue samples, thus facilitating comparative immunohistochemical studies.

Figure 8:
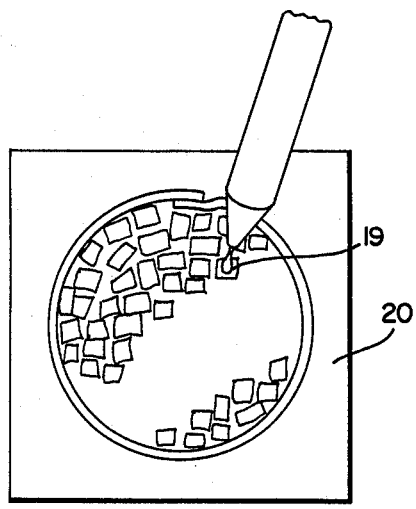
FIG. 8 is a schematic perspective view illustrating the application of a drop of a material to be tested, such as a hybridoma supernatant or an antiserum, to the surface of a section shown in FIGS. 6 and 7, for example, to stain the exposed cross-section of the specimen rods.
Figure 9:
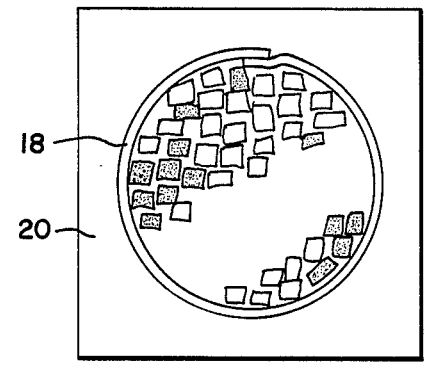
FIG. 9 is an elevational view schematically illustrating the staining of the exposed cross-sections of only some of the specimen rods in the section of tissue block of FIGS. 6, 7 and 8.

One of the applications of the present invention relates to immunohistological testing. As shown in FIGS. 8 and 9, a drop 19 of tissue reagent such as hybridoma supernatant or antiserum is applied to a slice of multi-specimen tissue block mounted on slide 20. The resulting immunostaining of certain individual tissue rods (darkened rods) may indicate the sensitivity and specificity of the antibody in the supernatant or antiserum for marker substance or antigen contained in the immunostained rods.

Figure 10:
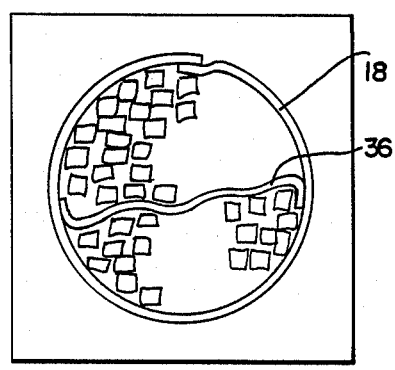
FIG. 10 is an elevational view of a section of tissue block which schematically illustrates the disposition of a septum in the casing to separate the space within the casing into two separate specimen rod compartments.

FIG. 10 shows a section 18 of a sausage which contains a septum 36 which divides the slice into two distinct compartments each of which can contain different groupings of specimen rods. Examples of such different groupings are adenocarcinomas, sarcomas, lymphomas, undifferentiated carcinomas, mesotheliomas and melanomas. A septum can be formed by wrapping casings around groups of rods to form individual "mini-sausages" which are then incorporated into a larger sausage. The resulting tissue blocks and slides are termed "segmented".

Figure 10B:
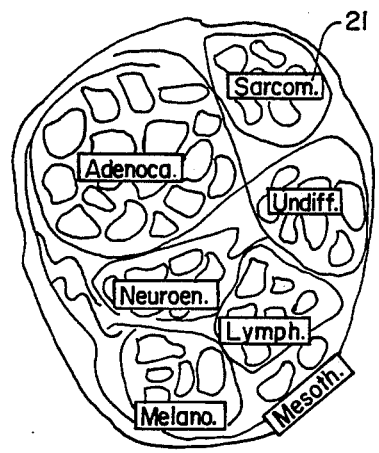
Figure 10A:

FIGS. 10(a) and 10(b) show another type of segmented sausage section. The sausage section of FIG. 10(a) was formed by segmenting the sausage as it was wrapped in its casing to create seven partitioned groups of adenocarcinomas, sarcomas, lymphomas, undifferentiated carcinomas, neuroendocrine carcinomas, mesotheliomas, and melanomas. The section was stained with a heterologous antiserum to protein S100 by the ABC (avidin biotin complex) immunohistochemical method, and counterstained with hematoxylin. Only the lower compartment containing six melonomas shows intense immunostaining. The advantage of using such segmented sections is that identification of a type of tissue or neoplasm is permitted due to its position in the section because histogenically related tissue specimens are grouped together as the segmented sausage is formed.

A further example of the use of segmented multi-specimen tissue blocks is depicted in FIG. 10(b). A map of a section of the sausage is drawn, and printed labels describing the particular tissues or neoplasms contained in each segment of the sausage are affixed to the corresponding segments of the section of the map. Thus, technicians and investigators with little or no expertise in tissue morphology can identify the tissue specimens and interpret the results of antibody screenings with little difficulty.

The present invention further comprises variants of multi-specimen tissue blocks and slides which are designed to serve specific purposes. Such variants include, among others, multipurpose segmented, theme oriented and clinically defined segmented tissue blocks and slides.

EXAMPLES

Miscellaneous (Multipurpose) Multi-Specimen Tissue Blocks

Multipurpose tissue blocks made according to the method of the present invention contain a broad array of well characterized neoplasms of varying histogenesis and degrees of differentiation. Typically, adenocarcinomas of various origins, and squamous cell, undifferentiated, and neuroendocrine carcinomas, lymphomas, melanomas, assorted sarcomas, as well as samples of uncommon neoplasms, are contained in such blocks. A wide spectrum of normal tissues may also be included in such a tissue block.

Figure 11:
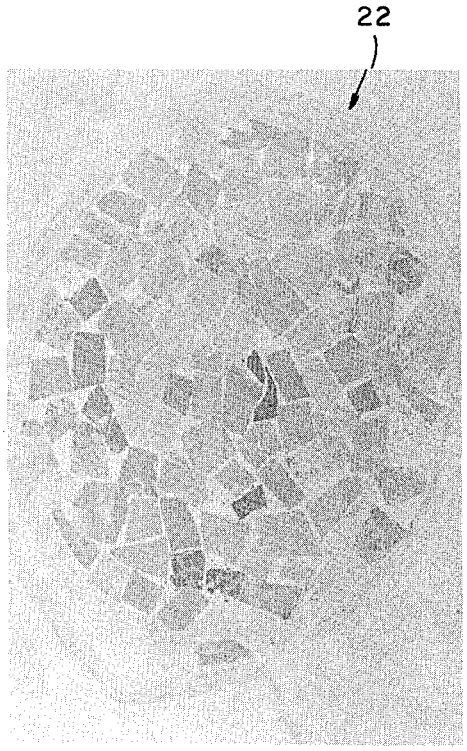
FIGS. 11 through 16 show actual stained sausage sections made pursuant to the invention as shown in FIGS. 1 through 10.

FIG. 11 shows a section 22 from a multipurpose tissue block comprising a broad variety of samples of neoplasms. The section 22 was immunostained by the ABC method with a drop of a hybridoma supernatant obtained from spleen lymphocytes of a mouse injected with human pancreatic carcinoma cells and counterstained with hematoxylin. Only four tissues, all gastrointestinal adenocarcinomas, show intense immunostaining indicating that monoclonal antibodies with some specificity for antigen or marker substance contained in or associated with the pancreatic carcinoma cells were present in the hybridoma supernatant.

Multipurpose tissue block sections are especially suitable for the screening of monoclonal antibodies in the early stages of hybridoma preparation. Tissue or tumor specificity, as well as any unexpected reactivity, can readily be detected by application of a single drop of hybridoma supernatant to a slide prepared from a section of a multipurpose tissue block.

Sections of multipurpose tissue blocks are also useful as controls for immunohistochemical studies conducted with many different antibodies. Because such sections contain tissues with several degrees of differentiation and with variable density of antigen expression, it is possible to control the sensitivity of each procedure and to monitor daily variations in the immunostaining method. Neoplasms with low reactivity can be identified in each section. Failure of such neoplasms to stain after an initial identification provides an indication that the sensitivity of the procedure has decreased and appropriate corrective measures can then be implemented.

Multipurpose tissue blocks can also be used for comparative studies of immunohistochemical methods, in particular for resolving questions concerning the relative sensitivity of immunochemical methods. Sections from such blocks are useful as "check samples" in surveys, e.g., for inexpensive comparisons of the results of immunohistochemical studies among various laboratories.

Figure 12:
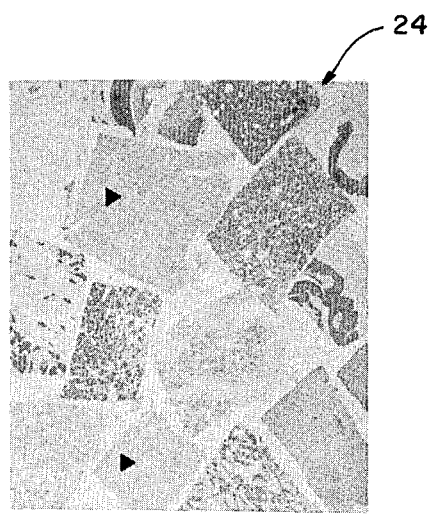

FIG. 12 is a close-up view, with a magnification of ten, of a portion of a multipurpose tissue block section 24 stained with a variety of monoclonal antibodies to low molecular weight keratins. The section 24 includes tissue specimens from fourteen different epithelial neoplasms. The specimens were stained in a conventional manner by the ABC method and were counterstained with hematoxylin. There is a marked variation in the stain intensity among the different tissues. Staining is particularly weak in two undifferentiated carcinomas which are indicated by arrows. Tissues of such low antigen density provide a routine sensitivity control.

Segmented Multi-Specimen Tissue Blocks

Figure 13:
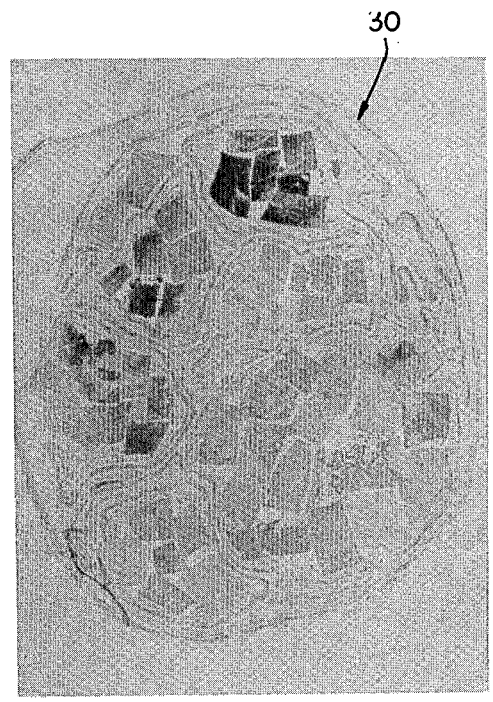

FIG. 13 depicts a section 30 of segmented multi-specimen tissue block prepared by wrapping groups of rods from "related" types of tumors or normal tissues into individual "mini-sausages", which are then incorporated in a larger sausage. Because histogenetically related tissues are grouped together, this arrangement permits identification of a type of tissue or neoplasm from its position in the section. Segmented tissue blocks permit technicians and investigators with no expertise in tissue morphology to interpret the results of antibody screenings with little difficulty.

Theme Oriented, Segmented Multi-Specimen Tissue Blocks

Figure 14:
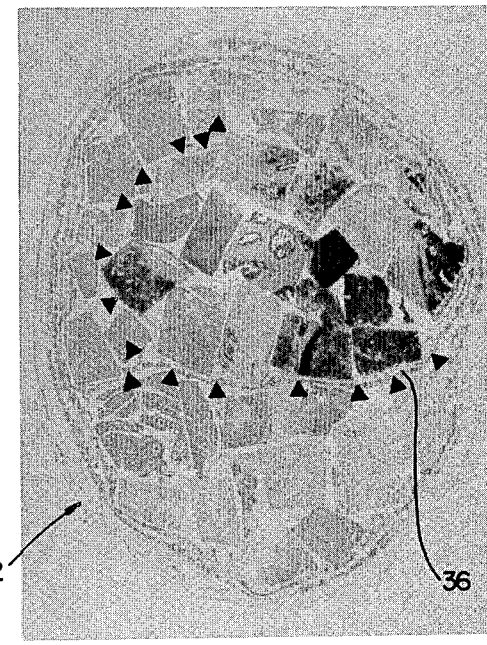

FIG. 14 depicts a section 32 of a theme oriented segmented multi-specimen tissue block. This block was constructed by segmenting the sausage as it was wrapped in its casing to create two or more partitioned groups of tissues or neoplasms which were selected for specific comparative studies. For example, a large group of neoplasms of a defined class, prostate carcinomas, occupies one segment of this multi-specimen tissue block, which makes such a segment useful for comparing prostate-specific monoclonal antibodies. Additional segments contain appropriate control specimens.

In FIG. 14, a septum 36 divides the specimens in section 32 into three compartments. The upper right compartment contains nineteen samples of prostatic tissues including well differentiated and poorly differentiated carcinomas. It also contains tissues of normal and hyperplastic prostate. The upper left compartment contains eight samples of neuroendocrine carcinomas of various degrees of differentiation. These carcinomas were chosen because of their histologic similarity to some prostatic carcinomas. The lower compartment contains twelve samples of non-prostatic adenocarcinomas of various origins. The section of FIG. 14 was immunostained with a monoclonal antibody directed against prostatic-specific antigens by the ABC method and counterstained with hematoxylin.

Figure 15:
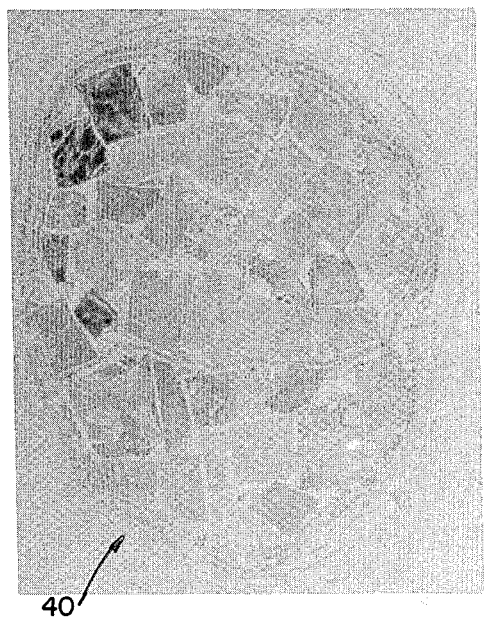

FIG. 15 shows a parallel section 40 of the same block from which section 32 of FIG. 14 was taken, which was magnified fourteen times. As a result, the tissues in the section 40 were substantially identical to the tissues in the section 32 of FIG. 14. The tissue specimens in section 40 were stained by the ABC method with a monoclonal antibody to neuron-specific enolase and counterstained with hematoxylin. Staining was intense for only some of the neuroendocrine carcinomas in the upper left compartment. Such a section is therefore useful to detect markers of neuroendocrine differentiation.

These theme oriented, segmented multi-specimen tissue blocks are particularly useful for further characterization of antibodies that have shown apparent specificity in screening against the multipurpose multi-specimen tissue block and as specificity and sensitivity controls for the markers for which they were designed.

Clinically Defined Multi-Specimen Tissue Blocks

Figure 16:
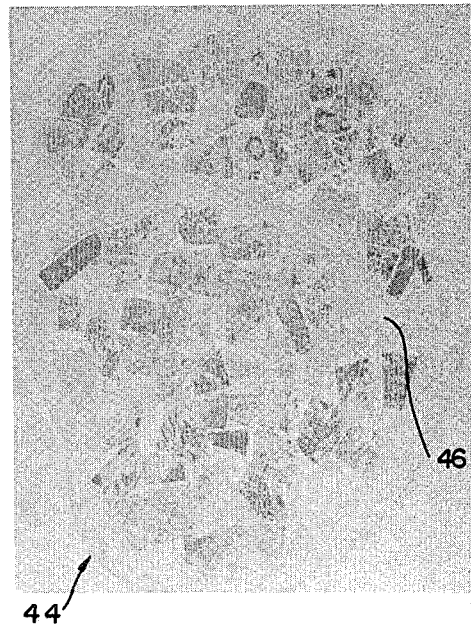

Blocks may be formed with tissue specimens disposed in clinically defined segments. FIG. 16 shows a section 44 magnified seven times that contained approximately ninety tumor samples from two groups of patients with stage I or stage II breast carcinoma. A single septum 46 separated the samples of the patients in one group from the patients in the other group. One group included tissues of stage I and stage II patients who developed metastases or had recurrences in less than two years after mastectomy. The other group was age-matched and stage-matched and its patients were free of disease after a long period of follow-up. The section was immunostained with a monoclonal antibody prepared against milk fat globule-derived membranes and lightly counterstained with hematoxylin. Twice as many tumor samples were stained by the monoclonal antibody in the first compartment as in the second compartment. This suggests that the antigen being detected may have prognostic significance.

I claim:

1. A method of preparing multi-specimen tissue block sections comprising:
    disposing a plurality of different antigenically reactive tissue specimens in the shape of rods having greater length than width in substantially parallel relationship on a casing;
    wrapping said specimen rods in said casing to form a specimen rod bundle;
    embedding said specimen rod bundle in embedding medium to provide a multi-specimen tissue block; and
    slicing said block to provide a plurality of sections each comprising a transverse cross-section of each of said tissue specimen rods in said specimen rod bundle.

2. The method of claim 1 in which said antigenically reactive tissues are fixed with tissue fixatives.

3. The method of claim 1 in which said antigenically reactive tissues are unfixed.

4. The method of claim 3 in which said unfixed tissues are freeze-dried.

5. The method of claim 2, 3 or 4 further comprising:
selecting said different antigenically reactive tissue specimens from those which are pre-embedded in a first water insoluble embedding medium in which said specimens are dehydrated;
processing said tissue specimens to remove said first embedding medium;
rehydrating said tissue specimens; and
forming said tissue specimens into specimen rods having greater length than width.

6. The method of claim 1 wherein said specimen rods have a transverse cross-sectional area of from about 0.5 to about 2.0 square millimeters and a length of approximately 10 millimeters.

7. The method of claim 1 wherein said specimen rod bundle is trimmed to expose said specimen rods in transverse cross-section prior to the embedding step.

8. The method of claim 1 wherein said casing is prepared from portions of the small intestines of small mammals.

9. The method of claim 1 wherein said casing is prepared from a sheet of organic material.

10. The method of claim 1 further comprising:
including at least one septum in said specimen rod bundle which divides said plurality of specimen rods into separate groups, and
thereafter wrapping said separate specimen rod groups in said casing to provide a specimen rod bundle having at least two groups of specimen rods separated by said septum.

11. The method of claim 10 wherein said septum is formed from said casing.

12. The method of claim 10 wherein said septum is formed by wrapping each separate group of specimen rods individually in a separate casings.

13. The method of claim 10 wherein said specimen rods in each of said separate groups of specimen rods have properties different from the properties of the specimen rods in the other groups.

14. The method of claim 13 in which tumor or neoplasm tissues are included in at least one separate group of specimen rods and control specimen rods are included in a different group.

15. The method of any of claims 1–4 or 6–14 wherein said embedding media is paraffin, celloidin, or epoxy resin.

16. The method of claim 1 further comprising:
selecting said different antigenically reactive tissue specimens from those which are either fixed or unfixed and freeze-dried, and pre-embedded; in a first embedding media selected from the group consisting of paraffin, celloidin or epoxy resin;
processing said tissue specimens to remove said first embedding media;
rehydrating said tissue specimens; and
forming said tissue specimens into specimen rods having greater length than width.

17. The method of claim 1 wherein said tissue block sections have a thickness of from about $2.5\mu$ to about $10\mu$.

18. A method as defined by any one of claims 10 to 14 in which at least one separate rod group includes rods of normal tissue and at least one other separate rod group includes rods of tumor tissues.

19. A method as defined by any one of claims 10 to 14 in which each separate rod group includes rods of different tumor tissues.

20. A method of preparing a multi-specimen tissue block, and sections thereof, comprising:
forming a plurality of different antigenically reactive tissue specimens into rods having a relatively small cross sectional area and a relatively great length;
disposing said rods in a substantially parallel relationship on a casing;
wrapping said rods in said casing;
embedding said wrapped rods in an embedding medium to form a tissue block; and
slicing said block into sections which each contain a cross-section of each of said rods.

21. The method of claim 20 wherein said tissue samples are fixed with a tissue fixative.

22. The method of claim 20 wherein said tissue samples are unfixed.

23. The method of claim 22 wherein said unfixed samples are freeze-dried.

24. The method of claim 21, 22 or 23 further comprising:
selecting said different antigenically reactive tissue specimens such that prior to the time that said specimens are formed into rods, said specimens have been pre-embedded in a first embedding media in which said specimens are dehydrated;
processing said tissue specimens to remove said first embedding media; and
rehydrating said tissue specimens.

25. The method of claim 20 in which said tissue block sections have a thickness of from about $2.5\mu$ to about $10\mu$.

26. The method of claim 20 in which the transverse cross-sectional area of each of said rods is from about 0.5 to about 1.5 square millimeters, and the length of said rods is approximately 10 millimeters.

27. A method comprising:
providing tissue specimens containing different marker substances;
forming said tissues into rods having a relatively great length and a relatively small cross-sectional area;
disposing said rods in a substantially parallel relationship on a casing; and
wrapping and securing said rods in said casing.

28. The method of claim 27 further comprising:
embedding said wrapped rods in an embedding medium; and
forming thin sections of said embedded wrapped rods wherein said sections are substantially parallel to the cross-sectional plane of said rods.

29. The method of claim 27 wherein said tissue specimens are unfixed and freeze-dried.

30. The method of claim 27 wherein said tissue specimens are fixed.

31. The method of claim 27 wherein said tissue specimens have been pre-embedded in an embedding medium prior to the time said tissue specimens are formed into said rods.

32. The method of claim 28 or 31 wherein said embedding medium is paraffin, celloidin, or epoxy resin.

33. A multi-specimen tumor tissue block containing a plurality of closely spaced, casing wrapped, parallel, generally rod shaped, different tumor tissue specimens containing reactive marker substances.

34. A microscopic slide bearing a plurality of small, closely spaced antigenically reactive tissue specimens bounded by a casing section.

35. A microscopic slide as defined by claim 34 in which said plurality of tissue specimens is divided into at least two segments by at least one septum.

36. A microscopic slide as defined by claim 35 in which at least one of said segments includes tumor tissue specimens.

37. A microscopic slide as defined by claim 35 in which at least one of said segments includes normal tissue specimens.

* * * * *

UNITED STATES PATENT AND TRADEMARK OFFICE
CERTIFICATE OF CORRECTION

PATENT NO. : 4,820,504

DATED : April 11, 1989

INVENTOR(S) : Hector A. Battifora

It is certified that error appears in the above-identified patent and that said Letters Patent is hereby corrected as shown below:

Column 1, line 4, after the title insert the following:

--This invention was made with government support under Grant No. R01 CA37194 awarded by the National Institutes of Health. The government has certain rights in the invention.--.

Signed and Sealed this

Second Day of March, 1993

Attest:

STEPHEN G. KUNIN

*Attesting Officer*     *Acting Commissioner of Patents and Trademarks*